(12) United States Patent
Borthakur et al.

(10) Patent No.: US 8,076,936 B2
(45) Date of Patent: Dec. 13, 2011

(54) REDUCING IMAGING-SCAN TIMES FOR MRI SYSTEMS

(75) Inventors: Ari Borthakur, Philadelphia, PA (US); Ravinder Reddy, Gladwyne, PA (US); Sridhar Charagundla, McLean, VA (US); Jyothsna Charagundla, legal representative, McLean, VA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 187 days.

(21) Appl. No.: 12/425,130

(22) Filed: Apr. 16, 2009

(65) Prior Publication Data

US 2009/0273343 A1 Nov. 5, 2009

Related U.S. Application Data

(63) Continuation of application No. PCT/US2007/022159, filed on Oct. 17, 2007.

(60) Provisional application No. 60/852,241, filed on Oct. 17, 2006.

(51) Int. Cl.
*G01V 3/00* (2006.01)
(52) U.S. Cl. .................... 324/307; 324/309
(58) Field of Classification Search .............. 324/307, 324/309
See application file for complete search history.

(56) References Cited

U.S. PATENT DOCUMENTS

| | | | |
|---|---|---|---|
| 5,245,282 A | 9/1993 | Mugler | |
| 5,786,693 A | 7/1998 | Gullapalli | |
| 6,836,114 B2 | 12/2004 | Reddy | |
| 6,885,193 B2 | 4/2005 | Foxall | |
| 7,064,545 B2 * | 6/2006 | Zaharchuk et al. | 324/307 |
| 7,116,104 B2 * | 10/2006 | Reddy et al. | 324/307 |
| 7,596,252 B2 | 9/2009 | Hasselberg | |

OTHER PUBLICATIONS

Borthakur, et al. "Three-dimensional T1r-weighted MRI at 1.5 Tesla." J Magn Reson Imaging 17(6):730-736 (2003).
Borthakur, et al. "In vivo measurement of T1rho dispersion in the human brain at 1.5 tesla." J Magn Reson Imaging 19(4):403-409 (2004).
Borthakur, et al. "A pulse sequence for rapid in vivo spin-locked MRI." J Magn Reson Imaging 23(4):591-596 (2006).
Charagundla, et al. "Off-resonance proton T1r dispersion imaging of 17O-enriched tissue phantoms." Magn Reson Med 39(4):588-595 (1998).
Dixon, et al. "Myocardial suppression in vivo by spin locking with composite pulses." Magn Reson Med 36(1):90-94 (1996).
Duvvuri, et al. Human knee: in vivo TI(rho)-weighted MR imaging at 1.5 T-preliminary experience. Radiology 220 (3):822-826 (2001).
Grohn, et al. "Early detection of irreversible cerebral ischemia in the rat using dispersion of the magnetic resonance imaging relaxation time, T1rho." J Cereb Blood Flow Metab 20(10): 1457-1466 (2000).

(Continued)

*Primary Examiner* — Louis Arana
(74) *Attorney, Agent, or Firm* — Montgomery, McCracken, Walker & Rhoads, LLP; Evelyn H. McConathy

(57) ABSTRACT

Provided are methods and systems for rapid MRI imaging-scanning that provides 2D or 3D coverage, high precision, and high-temporal efficiency, without exceeding SAR limits. In one embodiment, a pulse sequence process is performed that includes a $T_{1\rho}$ preparation period, followed by a very rapid image acquisition process, which acquires multiple lines of k-space data. The combination of $T_{1\rho}$ preparation and acquisition of multiple lines of k-space, allows scan times to be shortened by as much as 3- or 4-fold or more, over conventional MRI scanning methods.

14 Claims, 9 Drawing Sheets

OTHER PUBLICATIONS

Hulvershorn, et al. "T1rho contrast in functional magnetic resonance imaging." Magn Reson Med 54(5): 1155-1162 (2005).

Johannessen, et al. "Assessment of human disc degeneration and proteoglycan content using T1rho-weighted magnetic resonance imaging." Spine 31(11): 1253-1257 (2006).

Lamminen, et al. "T1rho dispersion imaging of diseased muscle tissue." Br J Radiol 66(789):783-787 (1993).

Li, et al. "In vivo 3T spiral imaging based multi-slice T(1rho) mapping of knee cartilage in osteoarthritis." Magn Reson Med 54(4):929-936 (2005).

Markkola, et al. "T1rho dispersion imaging of head and neck tumors: a comparison to spin lock and magnetization transfer techniques." J Magn Reson Imaging 7(5):873-879 (1997).

Mlyarnik, et al. "The role of relaxation times in monitoring proteoglycan depletion in articular cartilage." J Magn Reson Imaging 10(4):497-502 (1999).

Poptani, et al. "T1rho imaging of murine brain tumors at 4 T." Acad Radiol 8(1):42-47 (2001).

Santyr, et al. "Spin locking for magnetic resonance imaging with application to human breast." Magn Reson Med 12(1):25-37 (1989).

Scheffler, et al. "Principles and applications of balanced SSFP techniques." Eur. Radiol. 13:2409-2418 (2003).

Schmitz, et al. "Three-dimensional true FISP for high-resolution imaging of the whole brain". Eur Radiol 13 (7):1577-1582 (2003).

Wheaton, et al. "Correlation of T1rho with fixed charge density in cartilage." J Magn Reson Imaging 20 (3):519-525 (2004).

Wheaton, et al. "Pulse sequence for multislice T1rho-weighted MRI." Magn Reson Med 51(2):362-369 (2004).

Witschey, et al. "Artifactis in T1rho weighted imaging: Compensation for B1 and B0 field imperfections." JMR 186:75-85 (2007).

* cited by examiner

REDUCING IMAGING-SCAN TIMES FOR MRI SYSTEMS

CROSS-REFERENCE TO RELATED APPLICATIONS

This application is a continuation of International Application PCT/US2007/022159 filed on Oct. 17, 2007 and published on Apr. 24, 2008, which claims priority to U.S. Provisional Application 60/852,241 filed on Oct. 17, 2006, each of which is incorporated herein in its entirety.

STATEMENT OF GOVERNMENT INTEREST

This work was supported in part by National Institutes of Health grants R01AR4504, AR051041, and performed at a NIH supported resource center (NIH RR02305). The government may have certain rights in this invention.

FIELD OF THE INVENTION

The present invention relates to magnetic resonance imaging (MRI), and more particularly, a magnetic resonance (MR) pulse sequence for reducing imaging-scan times for MRI systems.

BACKGROUND OF THE INVENTION

MRI, or Magnetic Resonance Imaging, (including: spectroscopy, conventional, and fast imaging techniques) is viewed as a conventional medical procedure having acceptable risks and certain concerns regarding bio-effects and patient safety. Of these concerns, electromagnetic energy adsorption may result in a host of undesired effects such as tissue or cellular damage. Absorption of electromagnetic energy by the tissue is described in terms of Specific Absorption Rate (SAR), which is expressed in watts/kg. SAR in MRI is a function of many variables including pulse sequence and coil parameters and the weight of the region exposed. In the United States, for example, the recommended SAR level for head imaging is 8 watts/kg.

$T_{1\rho}$ is commonly referred to as the longitudinal relaxation time constant in the rotating frame. $T_{1\rho}$ MRI produces images with contrast different from conventional $T_1$- or $T_2$-weighted images. $T_{1\rho}$ relaxation is obtained by spin-locking the magnetization in the transverse plane with the application of a low power radio frequency (RF) pulse(s). $T_{1\rho}$ relaxation is influenced by molecular processes that occur with a correlation time, $\tau_c$, that is proportional to the frequency of the spin-lock pulse ($\gamma B_1/2\pi$). This frequency typically ranges from zero to a few kilohertz (kHz). In biological tissues, $T_{1\rho}$ is approximately $T_2$, the spin-spin relaxation time constant, for very low amplitude spin-lock pulses and increases with higher intensity $B_1$ fields. The sensitivity of $T_{1\rho}$ to low-frequency interactions facilitates the study of biological tissues in a manner that is unattainable by other MR methods. MRI using $T_{1\rho}$-weighted contrast has been used to investigate and assess the condition of a variety of tissues such as breast, brain, and cartilage.

Contrast in magnetic resonance (MR) images derives from the magnetic relaxation properties of tissues. Variations in tissue relaxation times help to distinguish the healthy and the pathological states. An unconventional contrast mechanism called "$T_{1\rho}$ imaging" shows sensitivity to the breast cancers, early acute cerebral ischemia, knee cartilage degeneration during osteoarthritis, posttraumatic cartilage injury, and the intervertebral discs among people with nonspecific lower back pain. In addition, functional $T_{1\rho}$ imaging shows an augmented signal to brain activation and oxygen consumption (metabolism), and other applications.

Time constraints during an MR clinical examination place certain restrictions on $T_{1\rho}$ imaging sequences. For example, to diagnose a patient presenting chronic knee joint pain requires a pulse sequence with full volume coverage of the articular cartilage of the patella, femoral condyle and tibial plateau.

Present, pulse sequences are insufficient, however, for a standard clinical examination, because of either incomplete anatomical coverage, or prohibitively-long scan durations. That is, present, single-slice, 2D Turbo Spin Echo (TSE)-based acquisition schemes require an acquisition time on the order of a couple of minutes per slice. This time quickly increases if multiple slices are required. Compounding the time issue is the fact that multiple acquisitions are required to generate $T_{1\rho}$ maps of the tissue. Spin-locked Echo-Planar imaging (SLEPI) has a much briefer scanning time for single slice imaging, but the non-selective spin-lock pulse used does not allow for 3D data acquisition. A multi-slice 2D sequence with an equivalent adjacent slice-spacing to a 3D acquisition would result in cross-talk between slices due to imperfect excitation pulse slice profiles and thin slices are not achievable. Since $T_{1\rho}$ mapping involves collection of at least four 3D data sets at varying SL times, it is inherently inefficient.

Conventional 3D fast gradient-echo (FGRE) MRI, multi-slice and 2D EPI-based sequences typically require 20-25 minutes for gathering a single $T_{1\rho}$ map. Still further, conventional 3D $T_{1\rho}$ maps are typically collected with 2-4 mm slice thickness, since it is too time consuming to collect 3D maps with isotropic voxel sizes. $T_{1\rho}$-weighted volume sets in clinical MRI studies examining pathologies in extended regions, such as, the articular surfaces of the knee joint, brain and heart, cannot be obtained under the time constraints of a viable clinical exam. Therefore, at least two views, e.g., sagittal and axial, are required to properly visualize anatomical structures in 3D $T_{1\rho}$ maps, which presently require a prohibitively long duration.

SUMMARY OF THE INVENTION

To solve these and other problems, the present invention described herein, introduces a method of, and system for, rapid MRI imaging-scanning that provides 2D or 3D coverage, high precision, and high-temporal efficiency without exceeding SAR limits.

In one embodiment, this is accomplished by using a pulse sequence process that includes a $T_{1\rho}$ preparation period followed by a very rapid image acquisition process, which acquires multiple lines of k-space data. The combination of $T_{1\rho}$ preparation and acquisition of multiple lines of k-space, allows scan times to be shortened by as much as 3 or 4-fold or more, over conventional scanning methods.

In one embodiment of the invention, the $T_{1\rho}$ pulse sequence includes five stages: a pre-preparation, $T_{1\rho}$ preparation, post-preparation, and image acquisition stages, and post image acquisition period which facilitates clinical imaging.

In addition to the decreased scan duration, there are other aspects of the invention. For instance, in yet another embodiment, the $T_{1\rho}$ preparation period is insensitive to magnetic field inhomogeniety. This is valuable, since magnetic field inhomogenieties can cause image artifacts and prevent accurate diagnoses.

In another embodiment, methods to reduce $T_{1\rho}$ image blurring and incorrect measurement of $T_{1\rho}$ relaxation times or enhance signal to noise, are performed by a post-processing filter, a variable-flip-angle acquisition method, and/or a Half-Fourier acquisition method. Additionally, scan time can still be further shortened by reducing the $T_{1\rho}$ relaxation delay as part of the post image acquisition period, while compensating for magnetization saturation.

The $T_{1\rho}$ pulse sequence of the invention may be adapted for use with a wide array of clinical assessments including, but not limited to: intervertebral disk pathology, tumors, study of Alzheimer's disease, neuro-degeneration, myocardial abnormalities, arthritis, joint injuries and abnormalities, heart disease, and scanning cartilage pathology.

Additional objects, advantages and novel features of the invention will be set forth in part in the description, examples and figures which follow, all of which are intended to be for illustrative purposes only, and not intended in any way to limit the invention, and in part will become apparent to those skilled in the art on examination of the following, or may be learned by practice of the invention.

BRIEF DESCRIPTION OF THE DRAWINGS

The detailed description is explained with reference to the accompanying figures. In the Figures, the left-most digit(s) of the reference number identifies the figure in which the reference first appears.

FIG. 2 needs to include post-image acquisition period.

FIGS. 6A and 6C show unfiltered signals, by ky and pixel size, respectively. FIGS. 6B and 6D show filtered signals, by ky and pixel size, respectively.

DETAILED DESCRIPTION OF EMBODIMENTS OF THE INVENTION

Reference herein to "one embodiment," "an embodiment," or similar formulations herein, means that a particular feature, structure, operation, or characteristic described in connection with the embodiment, is included in at least one embodiment of the present invention. Thus, the appearances of such phrases or formulations herein are not necessarily all referring to the same embodiment. Furthermore, various particular features, structures, operations, or characteristics may be combined in any suitable manner in one or more embodiments.

Figure 1:
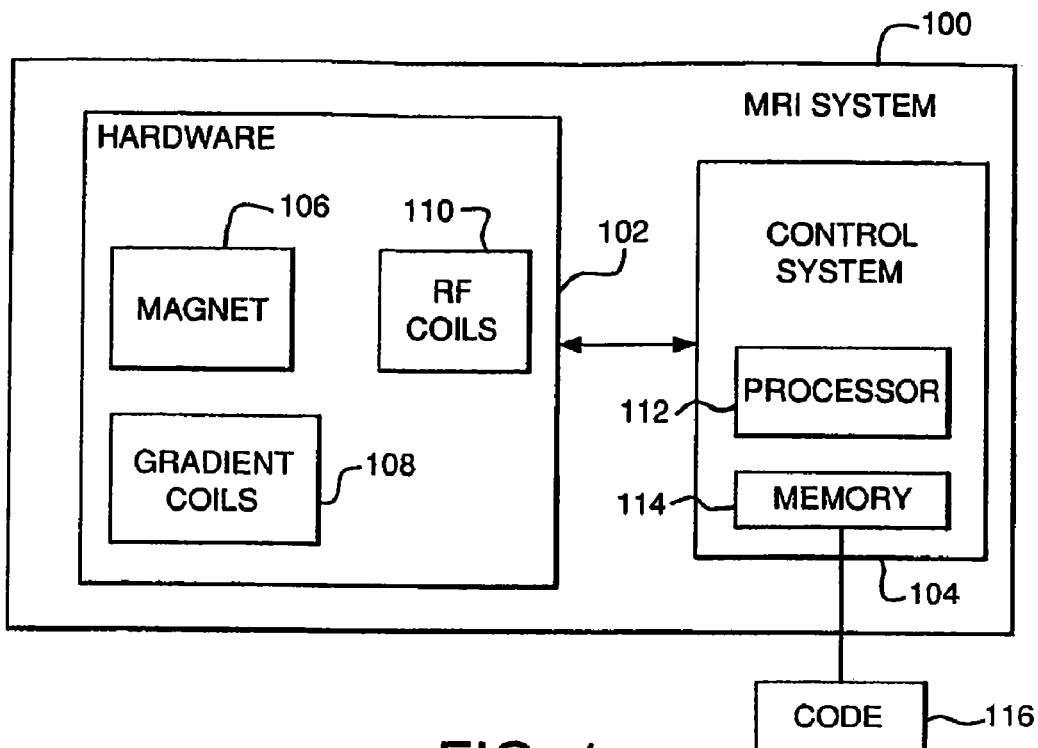
FIG. 1 illustrates an MRI system 100 within which the present invention can be either fully or partially implemented.

FIG. 1 illustrates an MRI system 100 within which the present invention can be either fully or partially implemented. As appreciated by those skilled in the art, there are various ways to implement an MRI system 100. In one possible embodiment, MRI system 100 includes hardware components 102, and a control system 104. As is well known by those skilled in the art, typical hardware components 102 include: a magnet 106 for producing a stable and very intense magnetic field, gradient coils 108 for creating a variable field, and radio frequency (RF) coils 110, which are used to transmit energy and to encode spatial positioning.

Control system 104 controls hardware components 102, such as the scanning sequencing operations, and processes information obtained from scanning. Control system 104 may be implemented as a computer or control device, which includes at least one processor 112, and memory 114. Memory 114 may include volatile memory (e.g., RAM) and/or non-volatile memory (e.g., ROM). It is also possible for other memory mediums (not shown) having various physical properties to be included as part of control system 104.

Control system B may also include code 116 stored in memory 114, such as software and/or firmware that causes MRI system 100 to perform scanning, and processing of images. Much of the discussion below will focus on embodiments for performing operations of control system 104—that may be embodied as code 116—used to control MRI system 100. In particular, the $T_{1p\rho}$ sequence used for issuing RF and gradient pulses, and image acquisition stages.

Figure 2:
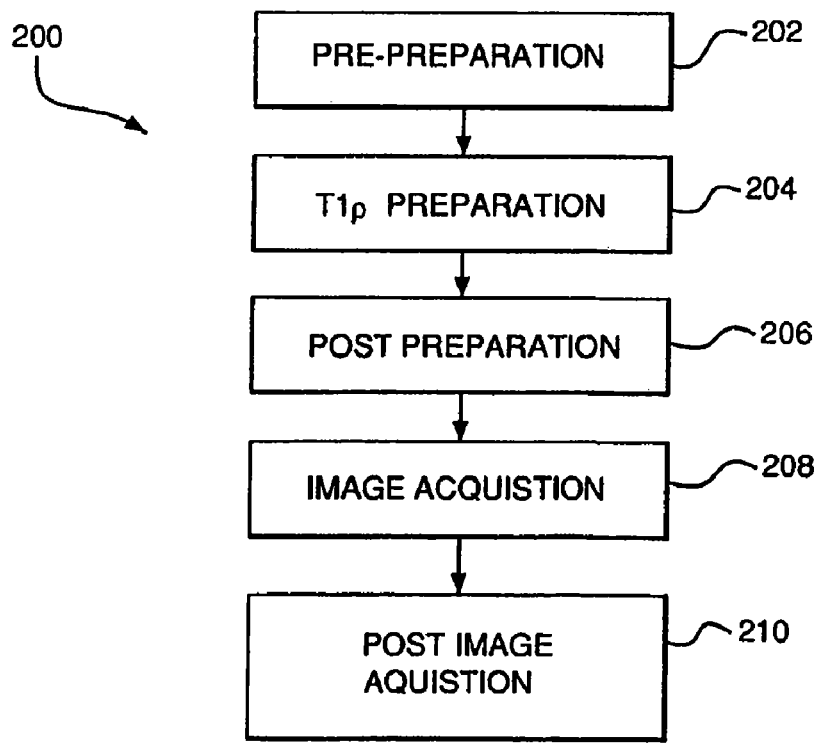
FIG. 2 is an exemplary method 200 for performing rapid MRI imaging-scanning through the use of an MRI system, such as system 100 of FIG. 1.

FIG. 2 is an exemplary method 200 for performing rapid MRI imaging-scanning through the use of an MRI system, such as system 100 of FIG. 1. Method 200 includes blocks 202, 204, 206, 208, and 210 (each of the blocks represents one or more operational acts). The order in which the method is described is not to be construed as a limitation, and any number of the described method blocks may be combined in any order to implement the method. Furthermore, the method can be implemented in any suitable hardware, software, firmware, or combination thereof. Additionally, although each module in FIG. 2 is shown as a single block, it is understood that when actually implemented in the form of computer-executable instructions, logic, firmware, and/or hardware, that the functionality described with reference to it may not exist as separate identifiable block.

In block 202, pre-preparation is performed. In one embodiment, pre-preparation involves several RF, gradient pulses and delays that may be activated at any time during a sequence to modify $T_{1\rho}$ contrast. It is appreciated by those skilled in the art after having the benefit of this disclosure that preparation periods may be used to complement $T_{1\rho}$ imaging in order to reduce blurring, artifacts, etc. These are not necessarily mutually exclusive from the image acquisition period. Examples of pre-preparation pulses include Inversion, Gradient Tagging, Diffusion-Weighting, and Spectral Excitation/Saturation.

A magnetization "inversion" block (typically an RF pulse with a flip angle of 180°) may be used to null signal from a certain tissue. One application is to reduce the signal from joint space fluid in the knee or fluid in the ventricles, which may wash-out or blur the $T_{1\rho}$ image contrast. Variations of this block can be used for saturation recovery (an RF pulse with a flip angle of 90° or any general flip angle).

"Gradient Tagging" refers to the use of gradients to tag the spatial MR signal to form grids to track a region over time.

"Diffusion-Weighting" refers to the use of gradients to yield sensitivity to diffusion processes.

"Spectral Excitation/Saturation" refers to the use of gradients to enhance or diminish sensitivity to magnetic nuclei precessing at different rates. This is commonly used to eliminate the signal from fatty tissues.

In block 204, $T_{1\rho}$ preparation is performed. $T_{1\rho}$ preparation involves instructing MRI system 100 to issue a series of RF pulses used to obtain $T_{1\rho}$ contrast. There are several variations of RF pulses used. A novel variation of one embodiment is the $\Delta B_0$ and $B_1$ insensitive sequence FIG. 3, which refocuses dephasing caused by magnetic field inhomogenieties. Both external magnetic field inhomogenieties $\Delta B_0$ and RF field inhomogenieties $B_1$ produce similar banding or shading artifacts in magnetic resonance images.

Figure 3:
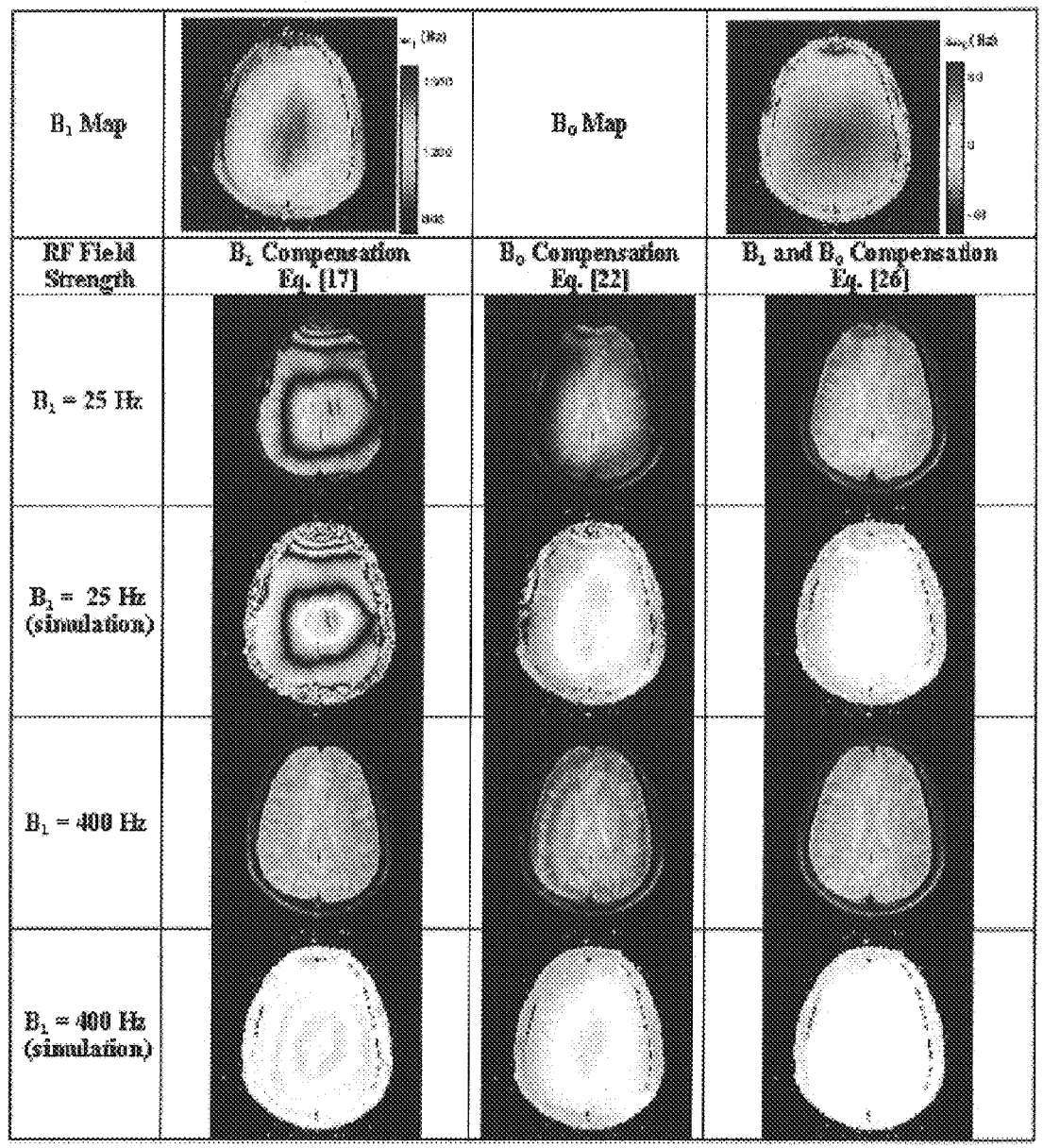
FIG. 3 shows $T_{1\rho}$ images of the brain at 3 Tesla using the methodology of the present invention.

Some of these artifacts are shown in FIG. 3 on the human brain, which shows $T_{1\rho}$ images of the brain at 3 Tesla. Low spin lock RF fields cause banding artifacts in traditional $T_{1\rho}$ sequences (listed $B_1$ Compensation and $B_0$ compensation above). To eliminate these artifacts a $B_1$-and-$B_0$-$T_{1\rho}$-preparatory sequence may be employed which is immune to both kinds of artifacts. More details of these variations are given in Witschey et al., "Artifacts in $T_{1\rho}$-weighted imaging: Compensation for $B_1$ and $B_0$ field imperfections." *JMR*186:75-85 (2007), incorporated herein by reference.

Figures 4A, 4B:
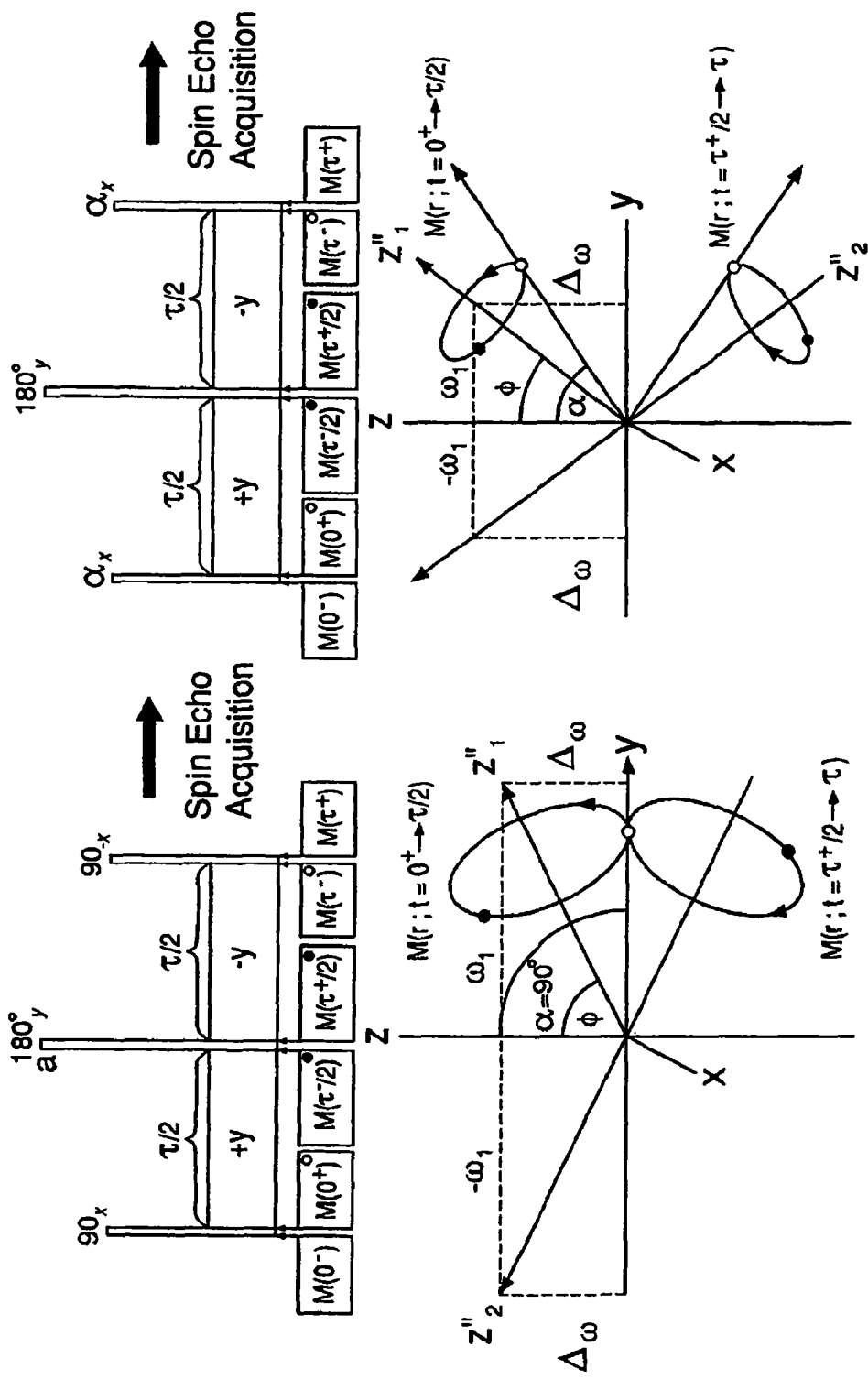
FIGS. 4A and 4B illustrate two alternate $T_{1\rho}$ preparation embodiments.

FIGS. 4A and 4B illustrate two alternate spin-acquisition embodiments. In the embodiment of FIG. 4A magnetization is flipped along the y-axis, where it nutates about the effective field (z'-axis) back along the y-axis. In the embodiment of FIG. 4B the magnetization follows a similar path, but with two differences: (1) the excitation flip angle does not need to be 90° and (2) $B_1$ insensitivity is maintained by flipping the magnetization along the −z-axis. The embodiment of FIG. 4B may be preferred over 4A, because it is insensitive to both external magnetic field inhomogenieties and RF field inhomogeniety.

Figure 5:
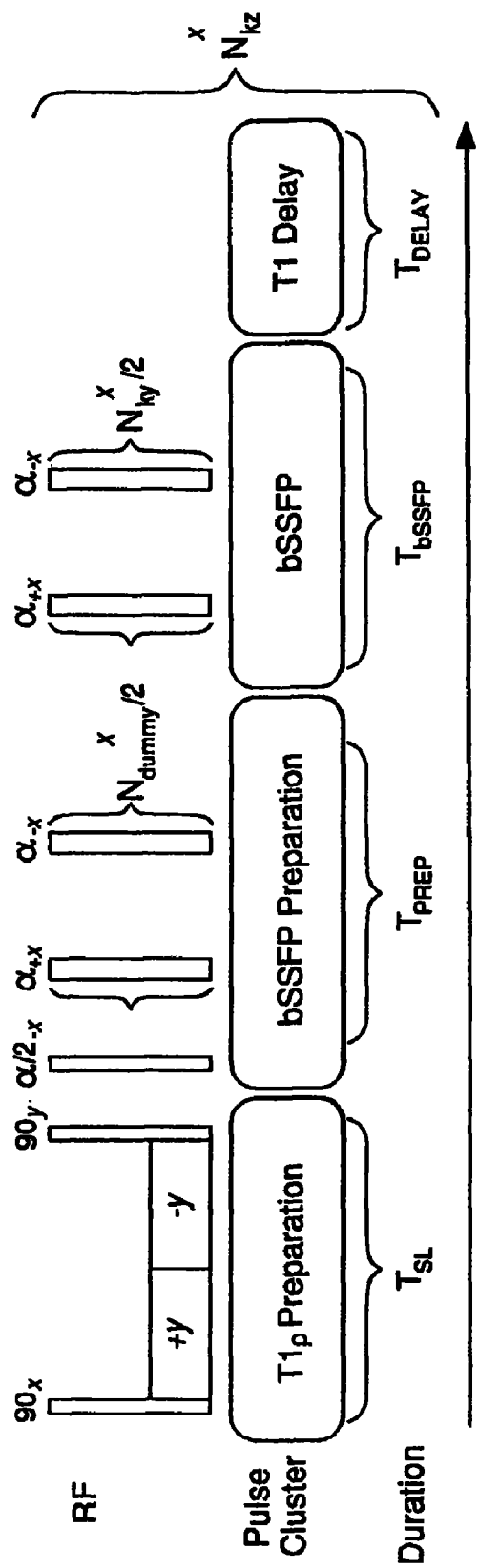
FIG. 5 shows an exemplary pulse sequence for $T_{1\rho}$-prepared balanced steady-state free precession for rapid 3D imaging.

Referring now to FIG. 5, is an exemplary pulse sequence for $T_{1\rho}$-prepared balanced-steady-state free precession for rapid 3D imaging. $T_{1\rho}$-weighted MRI uses a balanced gradient echo as illustrated in FIG. 5. "Balanced" means the transverse phase of magnetic nuclei due to gradient pulses (i.e., gradient moment) is zero at the end of each repetition time (TR).

One way to achieve $T_{1\rho}$ contrast is to apply a 90° pulse with an arbitrary initial phase flip of the initial magnetization into the transverse plane where it is spin-locked by a pair of rotary echo pulses (phase ±90 degrees to the initial pulse) which provide $T_{1\rho}$-weighting to the initial magnetization $M_0$. The duration or amplitude of the spin-locking pulse determines the final $T_{1\rho}$ contrast in the image. Following the spin-lock period, the magnetization is flipped longitudinally by another 90° pulse (phase 180° to the initial pulse). The $T_{1\rho}$-prepared magnetization is stored for image acquisition using the balanced gradient echo (bSSFP) sequence. Those skilled in the art, will appreciate that the angle of the pulse is not restricted to a 90° pulse for the flip angle in light of this disclosure.

An initial bSSFP preparation period is used prior to image acquisition to reduce artifacts caused by blurring caused by the transient echo amplitudes during the initial bSSFP image acquisition. The initial bSSFP preparation period consists of an α/2 pulse (phase 0) used to prevent oscillations of the transient echo amplitudes during the image acquisition period. Following this a pulse, any number of dummy pulses of phase alternating (±0) α pulses is applied to pulse the magnetization toward the steady-state. The loss of the initial $T_{1\rho}$-prepared magnetization depends on the flip angle of the α pulses, the repetition time (TR) and spin-lattice $T_1$ and spin-spin $T_2$ relaxation times. To achieve optimal $T_{1\rho}$-weighting, there are no dummy pulses following the initial $T_{1\rho}$ preparation period.

Next phase alternating (±0) α pulses are used to acquire the $T_{1\rho}$ prepared magnetization. The image acquisition gradients consist of both frequency and phase encoding gradients to acquire the k-space data. In this example, the echo amplitudes are recorded using a rectilinear k-space acquisition with frequency-encoding performed in the x-direction and phase encoding performed in the y- and z-directions.

Finally, the magnetization is restored to $M_0$ by a $T_1$ relaxation delay period where no RF pulsing occurs.

While FIG. 5 shows a specific example of rapid $T_{1\rho}$ image acquisition, it should be understood by those skilled in the art, after having the benefit of this disclosure, that the combination of a $T_{1\rho}$ preparation period with any rapid image acquisition technique is a part of the present invention. Thus, many modifications to the pulse sequence shown in FIG. 5 achieve the same result of rapid $T_{1\rho}$ image acquisition. Some examples of generalizations of the pulse sequence are explained here.

"Gradient Echo" refers to the balanced gradient echo (bSSFP) shown in FIG. 5 is only one example of the more general gradient echo. Gradient echoes, both spoiled and unspoiled, which spoil or refocus the gradient moment are equally valid techniques for rapid image acquisition. Any rapid gradient echo sequence consists of a series of RF pulses during which the so-called 'gradient echo' is used to acquire k-space data. This technique has multiple names: SPGR, FFE, FLASH, FISP, SSFP, FIESTA, CISS, DESS, as well other names.

By definition, the gradient echo uses a gradient to dephase the magnetization in the transverse plane with a gradient dephaser pulse, followed by a gradient rephaser during which k-space data is acquired with the MR hardware. The technique for gradient echo image acquisition consists of both phase and frequency encoding to 'encode' the spatial magnetization in k-space. The encoding is reconstructed using a technique, such as the fast Fourier Transform to create an image.

The RF pulses in the gradient echo sequence can be phase cycled to reduce artifacts or adjust the image contrast. A specific example of gradient echo RF pulses is a phase cycling routine, which causes RF spoiling of transverse magnetization. By rotating the phase of the RF pulse each acquisition period, the transverse magnetization accumulates an arbitrary phase each period and can cancel the transverse magnetization from a previous period. This technique is useful for preventing steady-state artifacts.

Following the acquisition of the k-space data during a repetition period, the gradient moment can be refocused (balanced) or spoiled. Either technique can be used, however, in the exemplary embodiment, the balanced-gradient-echo technique is used, because it achieves higher signal than spoiled gradient echo techniques. Balanced gradients refocus the gradient moment of transverse magnetization each repetition time, while spoiled gradients further dephase the transverse magnetization by a large gradient.

Rapid "spin echo acquisition" is obtained by modifying the gradient echo sequence above to refocus magnetic field inhomogeniety by the use of a refocusing RF pulse. This technique has multiple names: Carr-Purcell Meiboom Gill Spin Echo, Fast Spin Echo, Turbo Spin Echo (TSE). Specifically, a RF pulse is used to generate transverse magnetization. Because of local magnetic field inhomogeneities, the transverse magnetization is dephased. However, if a refocusing pulse is used at a time TE/2, at a later time TE, an echo is created by rephased magnetization.

"Half-Fourier acquisition" is used to acquire a partial set of k-space data. This can also be used to increase the signal to noise ration (SNR) and reduce blurring by simultaneously increasing the flip angle during image acquisition.

Regarding "Variable Flip Angle Image Acquisition," the flip angle of the gradient or spin echo image acquisition train may be varied to maintain $T_{1\rho}$ contrast and prevent imaging artifacts. One such application is to reduce blurring caused by the approach to the steady-state by repeated RF pulsing. Having explained the $T_{1\rho}$ preparation of block 204, it is now possible to discuss blocks 206 and 208.

Referring back to FIG. 2, in block 206 post preparation is performed. Post preparation involves generally the same pulsing as is performed with pre-preparation (see the discussion above with respect to block 202 above).

In block 208, image acquisition is performed. Image acquisition is obtained using a very rapid gradient echo or spin echo acquisition technique. Instead of acquiring only a single line of k-space data, a rapid image acquisition technique can acquire any number of lines of k-space data following the initial $T_{1\rho}$ preparation of block 204 (FIG. 2). This allows the scan time to be substantially shortened. If, for example, 128 lines of k-space are acquired immediately following the $T_{1\rho}$ preparation, then the scan time is shortened by 128-fold. This technique is especially suitable for clinical imaging, where patient motion or comfort is prohibitive.

In block 210 there is a post image acquisition period. Examples of post-image acquisition periods include T1 relaxation delays, or storage pulses. See also the discussion below. Exemplified in block 210 is the post image acquisition delay. It is possible to further accelerate the image acquisition by shortening the $T_1$-delay in FIG. 6. T1-delays are important to fully recover the magnetization to return to its equilibrium distribution. This can take as long as 2-4 seconds, depending on the tissue. It is possible to substantially shorten the $T_1$-delay (for example, to 0.3-0.4 seconds), shortening the scan time by another eight-to-ten fold. However, a model for magnetization saturation must be used to obtain the corresponding $T_{1\rho}$ contrast. One such model can be calculated for $T_{1\rho}$ magnetization in the steady-state after repeated $T_{1\rho}$ preparation periods. The model depends only on the $T_1$, $T_2$, flip angle and image acquisition techniques, but has been implemented for 3D $T_{1\rho}$ imaging.

To reduce blurring a k-space filter may be used to correct a non-constant echo amplitude during image acquisition as shown in the embodiment of FIG. 6A-6D. The filter design of FIGS. 6B and 6D compensates for the transient signal during bSSFP acquisition of $T_{1\rho}$ magnetization.

As a result of using method 200, time constraints during an MR clinical examination are eliminated. For example, prior to the invention, $T_{1\rho}$ imaging in a patient presenting chronic knee joint pain required a pulse sequence with full volume coverage of the articular cartilage of the patella, femoral condyle and tibial plateau. Two conventional choices are superior to others, a $T_{1\rho}$ prepared 2D multislice fast spin echo sequence or a $T_{1\rho}$ prepared 3D gradient echo $T_{1\rho}$ imaging sequence. Still both sequences are insufficient for a standard clinical examination with incomplete volume coverage or unreasonably long scan times.

The sequence of method 200 obviates these slower conventional sequences. To be more specific, conventional sequences acquire only a single line of k-space data after the initial $T_{1\rho}$ preparation period. This is because only a single gradient echo or spin echo is acquired following the initial $T_{1\rho}$ preparation.

In accordance with the present invention, multiple RF pulses (2 or more, and likely 128 or 256 pulses), gradient echoes or spin echoes are used to acquire the k-space data as in method 208. There are numerous ways to acquire k-space space data, including, but not limited to, Cartesian, radial or spiral acquisitions. This technique rapidly accelerates the time for image acquisition and the scan time is shortened proportional to the number of k-space lines that are acquired following the initial $T_{1\rho}$ preparation.

Figure 6:
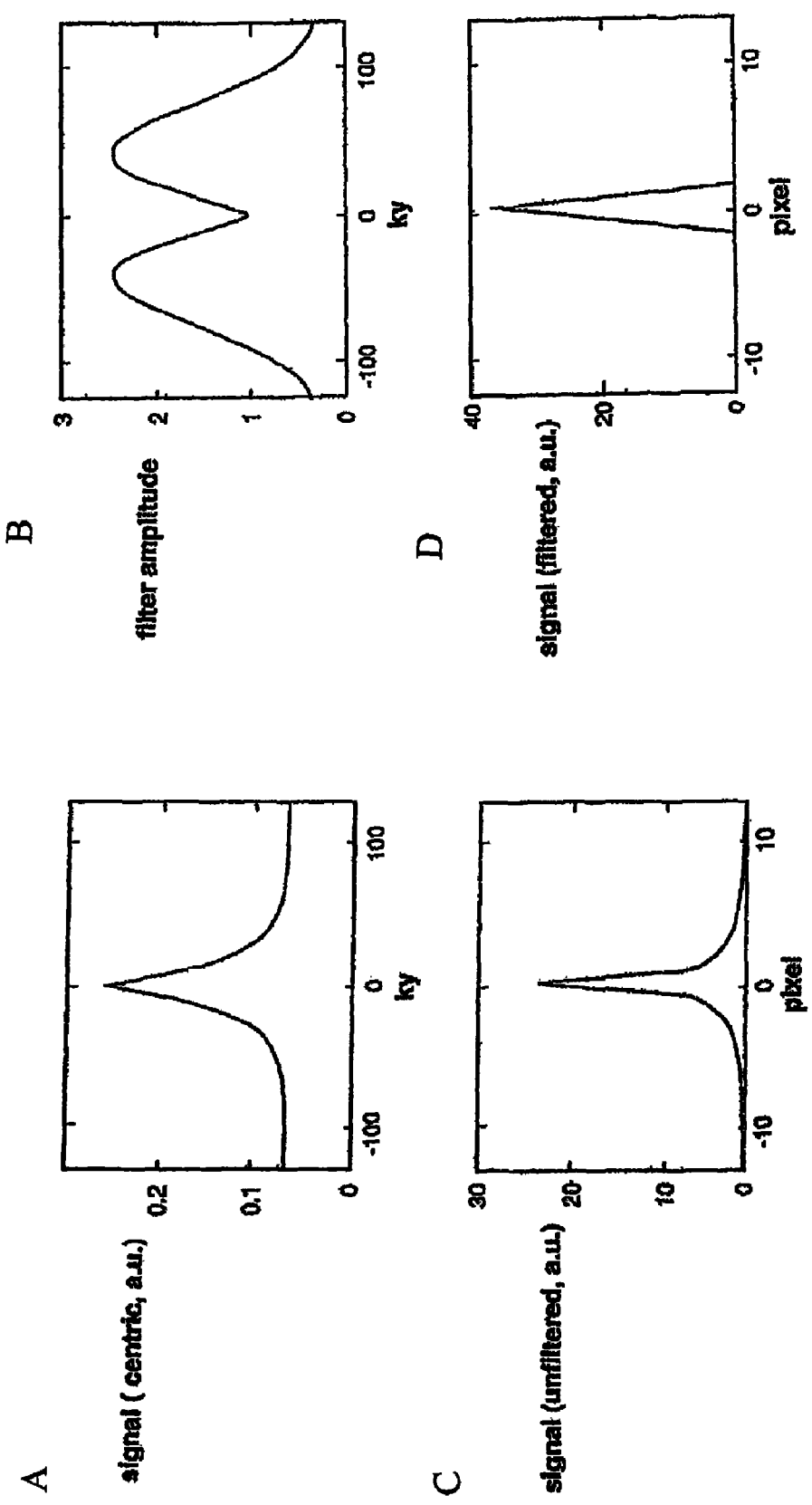
FIGS. 6A-6D show an exemplary k-space filter used to reduce blurring during image acquisition. The filter design compensates for the transient signal during bSSFP acquisition of $T_{1\rho}$ magnetization.

It is possible to further accelerate the image acquisition by shortening the $T_1$-delay in FIG. 6. $T_1$-delays are important to fully recover the magnetization to return to its equilibrium distribution. This can take as long as 2-4 seconds, depending on the tissue. It is possible to substantially shorten the $T_1$-delay (for example, to 0.3-0.4 s), shortening the scan time by another eight-to-ten fold, however, a model for magnetization saturation must be used to obtain the corresponding $T_{1\rho}$ contrast. One such model can be calculated for $T_{1\rho}$ magnetization in the steady-state after repeated $T_{1\rho}$ preparation periods. As above, the model depends only on the $T_1$, $T_2$, flip angle and image acquisition techniques, but has been implemented for 3D $T_{1\rho}$ imaging.

Another feature of the $T_{1\rho}$ acquisition is the use of multiple spin lock amplitudes or durations to generate parametric maps. Two such examples are a $T_{1\rho}$ map measuring the spatial $T_{1\rho}$ relaxation times or the spatial distribution of the signal obtained at a ratio of different spin lock amplitudes.

Another feature of the $T_{1\rho}$ acquisition is the use of exogenous contrast agents to complement or enhance the $T_{1\rho}$ contrast. Two such examples are inhaled magnetic molecular oxygen ($^{17}O_2$) or paramagnetic contrast agents, such as Gd-DTPA.

The foregoing can also be surmised as follows: a balanced Steady-State Free Precession (bSSFP) technique of rapid image acquisition of single-slice, multi-slice, or three-dimensional images and has been found to be an exceptional pulse sequence candidate for imaging articular cartilage, especially in patients with osteoarthritis. This sequence is also commercially named true fast imaging with steady precession (True-FISP), balanced fast field encoding (bFFE), and fast imaging employing steady-state excitation (FIESTA). In its conventional version, the bSSFP pulse sequence consists of a series of excitation pulses of alternating phase, each followed by a gradient-echo readout, and is capable of generating images with contrast based on the ratio $T_2/T_1$. Except, here a method for acquiring $T_{1\rho}$-weighted three-dimensional volumes in a time-efficient manner by using spin-lock pulses in conjunction with the bSSFP technique in a new pulse sequence is called SLIPS (Spin-Locked Imaging with Precession in the Steady-state). The signal expression of the new sequence was simulated and actual $T_{1\rho}$ measurements were performed in a homogeneous phantom of known $T_{1\rho}$, as well as in vivo in the human knee joint to map $T_{1\rho}$ in cartilage.

Figure 7:
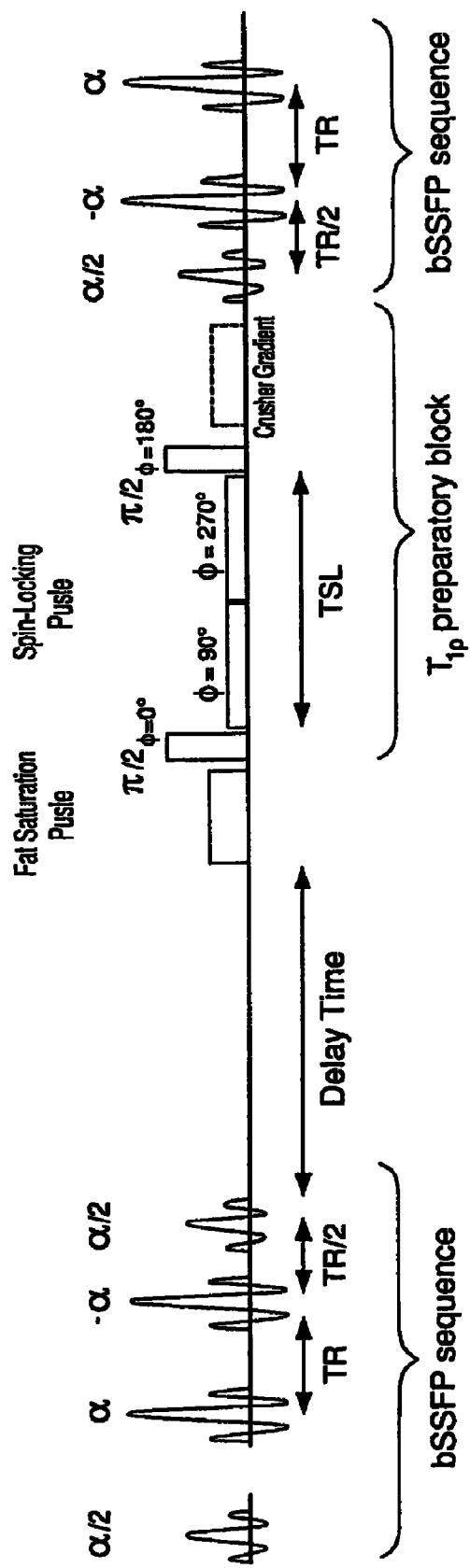
FIG. 7 shows another exemplary pulse sequence for $T_{1\rho}$-weighted MRI, a spin-locking pulse cluster, consisting of two anti-phase spin-locking lobes surrounded by alternate phase 90° RF pulses, including a pre-preparation (fat saturation), post-preparation ($\alpha/2$), balanced steady-state free precession (bSSFP) image acquisition, and post image acquisition (relaxation delay) periods.

Pulse sequence design. FIG. 7 shows a pulse sequence in accordance with another embodiment of the invention. A fat saturation pulse was applied in each segment to attenuate signal from fat in the marrow of the knee joint during in vivo experiments. $T_{1\rho}$ contrast was generated by applying a four-pulse cluster during each segment after fat-saturation. In this pulse cluster, a non-selective $\pi/2$ pulse excites spins into the transverse plane that are then spin-locked by the application of two phase-alternating (±90° phase-shifted from the phase of the first $\pi/2$ pulse) SL pulses. Phase-alternating SL pulses have been previously demonstrated to reduce image artifacts resulting from $B_1$ inhomogeneity. The duration of the SL pulses is denoted as TSL and typically ranges from a millisecond to ~50 mseconds for in vivo imaging. A delay of 20 μseconds was maintained between the SL pulse segments hardware switching between RF pulse excitations. A second non-selective $\pi/2$ pulse then returns the magnetization to the longitudinal axis.

For imaging the $T_{1\rho}$-prepared signal, a sequence of excitation pulses and gradient echo sampling are used to acquire the segment of k-space. The first excitation pulse has angle $\alpha/2$, and the following pulses have angle, $\alpha$, with alternating phase, until the final pulse, which has angle $\pi/2$. Each of these excitation pulses is separated by a time defined as "short repetition time" (Short TR). Once the whole segment of k-space has been acquired, the magnetization is allowed to relax toward thermal equilibrium for a time defined as "long repetition time" (Long TR). This acquisition method is then repeated for each subsequent segment in k-space until the whole volume has been acquired.

The bSSFP acquisition of Spin-Lock prepared magnetization signal greatly reduces scan time, but also increases the complexity of the weighting of the signal as compared to TSE-based spin-locking sequences. To begin with, the short TR approximation of the steady-state signal generated by bSSFP is given by Equation 1:

$$M_\infty = \frac{M_0 \sin\theta}{(T_1/T_2)(1-\cos\theta)+(1+\cos\theta)} e^{-TE/} \qquad \text{[Equation 1]}$$

The equation shows a $T_1/T_2$-weighting that is typical in bSSFP images. The addition of SL pulses does not result in an additional multiplicative factor to this equation (as it does with the single-slice TSE-based and EPI-based methods). A complicated signal expression arises from the fact that the prepared magnetization and steady-state magnetization are not directly related to each other. The reason for this is that the preparatory RF pulses (e.g., fat-saturation, $T_{1\rho}$ preparation, etc.) have the greatest effect on the magnetization immediately after their application, while the steady-state magnetization is produced only after a long period of repetitive pulsing. For this reason, the magnetization gradually reduces from a $T_{1\rho}$-prepared to a steady-state value in the SLIPS pulse sequence.

Example

Materials And Methods: A MRI "phantom" and two healthy male volunteers were imaged on a 1.5 T Sonata Siemens clinical MRI scanner (Siemens Medical Solutions, Erlangen, Germany) using an eight-channel knee coil (MRI Devices Corp., Muskego, Wis.). The phantom consisted of gel of 2% (w/v) agarose in phosphate-buffered saline (Sigma-Aldrich, St. Louis, Mo.) doped with 0.2 mM $MnCl_2$ to reduce $T_1$. For this particular study, only healthy subjects were studied without any clinically meaningful acute or chronic medical problems.

Estimation of $T_{1\rho}$ in agarose phantoms: The ability of pulse sequence to estimate accurate $T_{1\rho}$ values was evaluated using two agarose bottle phantoms. A series of $T_{1\rho}$-weighted images were acquired with the pulse sequence at seven spin-lock durations (TSL) (1, 5, 10, 20, 30, 35, and 40 mseconds). Other imaging parameters were TE=2.5 mseconds, short TR=5 mseconds, FOV=180 mm, 256×128 matrix size with 4 mm-thick sections and spin-locking frequency at 400 Hz. The parameter long TR was varied to determine its dependence on the resulting calculated $T_{1\rho}$ values. Circular regions of interest (ROI) were manually selected by a single user in each phantom. Identical ROIs were applied for all scans of the same phantom. Mean intensity values were calculated within the ROI and the results were fit to Equation 1 to generate an exponential decay rate with respect to TSL.

Estimation of $T_{1\rho}$ in the human knee articular cartilage: The utility of the pulse sequence to generate meaningful and accurate $T_{1\rho}$ maps in vivo was evaluated. Each subject's left knee was imaged by placing the knee in the coil, and padding was placed to restrict motion during the scan. A series of $T_{1\rho}$-weighted images were acquired with pulse sequence at five spin lock durations (1, 10, 20, 30, and 40 mseconds). The TE and short TR parameter values used were calculated for the minimum possible values under SAR limitations. Therefore, TE varied between 2.5 and 3.0 mseconds, and short TR was exactly twice the TE value. However, within each series, the two parameters were kept constant. Other imaging parameters were long TR=1 second, FOV=140 mm, 256×128 matrix size with 4 mm-thick slices, and a spin-locking frequency fixed at 400 Hz. Each data set (one per TSL) was smoothed using a 3×3×3 averaging matrix. These data sets were then used to generate $T_{1\rho}$ "maps" by fitting signal intensities as a function of TSL by linear regression to Equation 1. In the fitting routine, pixels whose intensities correlated poorly (i.e., $R^2<0.98$) with the equation were set to zero.

The calculated $T_{1\rho}$ values from these maps were verified by comparing them to single-slice $T_{1\rho}$ maps of the center slice of the acquisition volume obtained with a 2D TSE-based $T_{1\rho}$ pulse sequence. These images were acquired with the same FOV, slice thickness, and image dimensions as the T1ρ images images. In all, each MRI exam was conducted in less than thirty minutes, including a scout image and full collection of two views (sagittal and axial) with a set of five TSLs per view and imaging matrix of 256×128.

Data Processing: The images were transferred to a Dell Inspiron computer (Dell Inc., Round Rock, Tex.) for processing. Phantom and human knee images were processed in custom-written software in the IDL programming language (RSI Corp., Boulder, Colo.). Measurements of $T_{1\rho}$ relaxation times were performed on the entire FOV of the images. Measured values of $T_{1\rho}$ in the articular cartilage made with both the SLIPS and SL-TSE sequences were overlaid onto $T_2$-weighted images (FIG. 4). To increase consistency of comparison of scans between the same patient, IDL codes were used to co-register and realign images.

Figure 8:
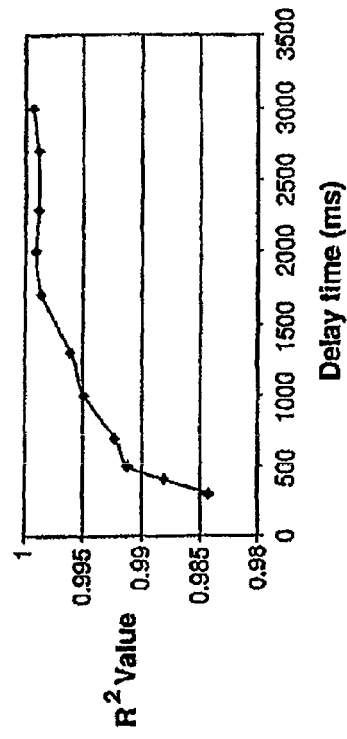
FIGS. 8A and 8B show calculated $T_{1\rho}$-values (FIG. 8A) obtained with the pulse sequence on an agarose gel phantom as a function of delay-time parameter. Also shown in FIG. 8B are the $R^2$ values of the exponential fits per Equation 1. This offers an example of a parametric mapping technique.
Figure 8:
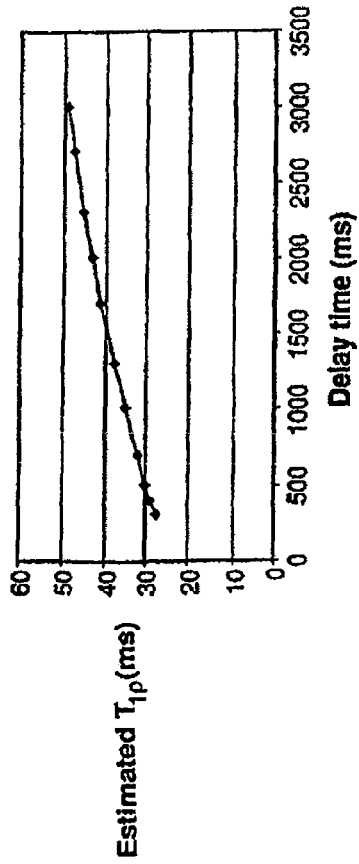

Results: FIG. 8A shows plots of calculated $T_{1\rho}$ values for the agarose phantoms and FIG. 8B shows the resultant R-squared values of the exponential fits, respectively. As can be seen, as long TR was increased, calculated $T_{1\rho}$ values for the phantom increased, and the R-squared value of the fit approaches the ideal value of 1.

Figure 9:
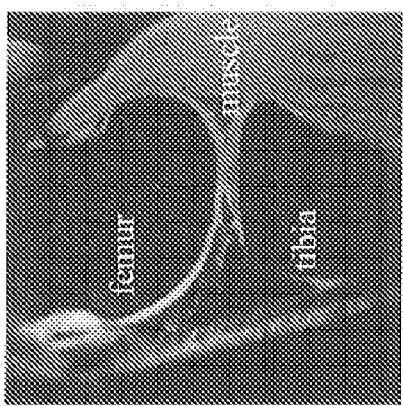
FIGS. 9A and 9B show images of the knee joint of a healthy volunteer acquired with the sequence and illustrate another example of the parametric mapping technique. The anatomy of the knee joint (bright signal from cartilage and synovial fluid, dark signal from bones such as the femur, tibia and patella) is clearly visible in the early spin lock duration images in both the sagittal (FIG. 9A) and axial (FIG. 9B) views. The long spin lock duration images show decreased signal in the cartilage of interest while signal from fluid remains strong due to its long $T_{1\rho}$.
Figure 9:
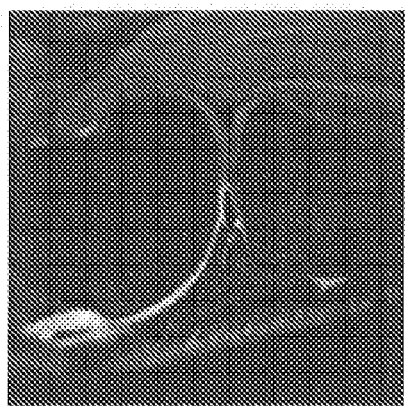
Figure 9:
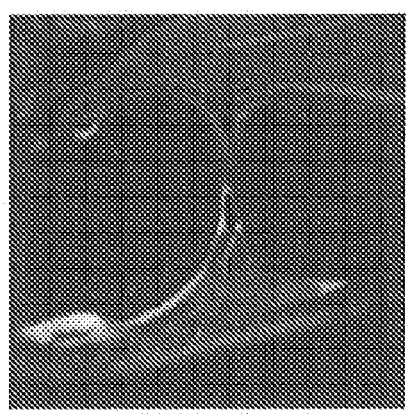
Figure 9:
Figure 9:
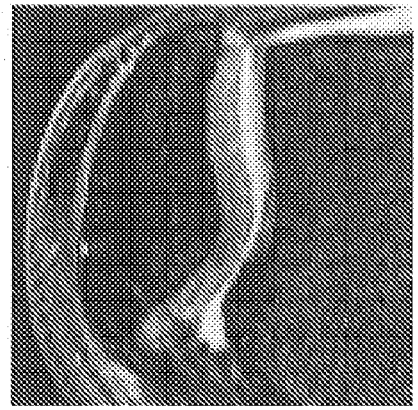
Figure 9:
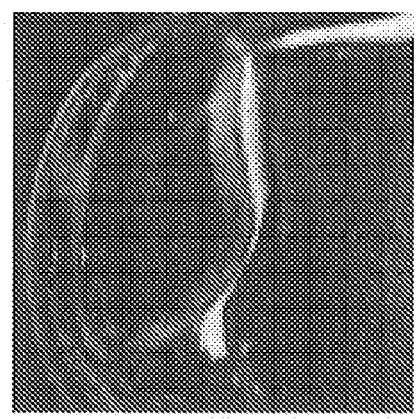
Figure 10:
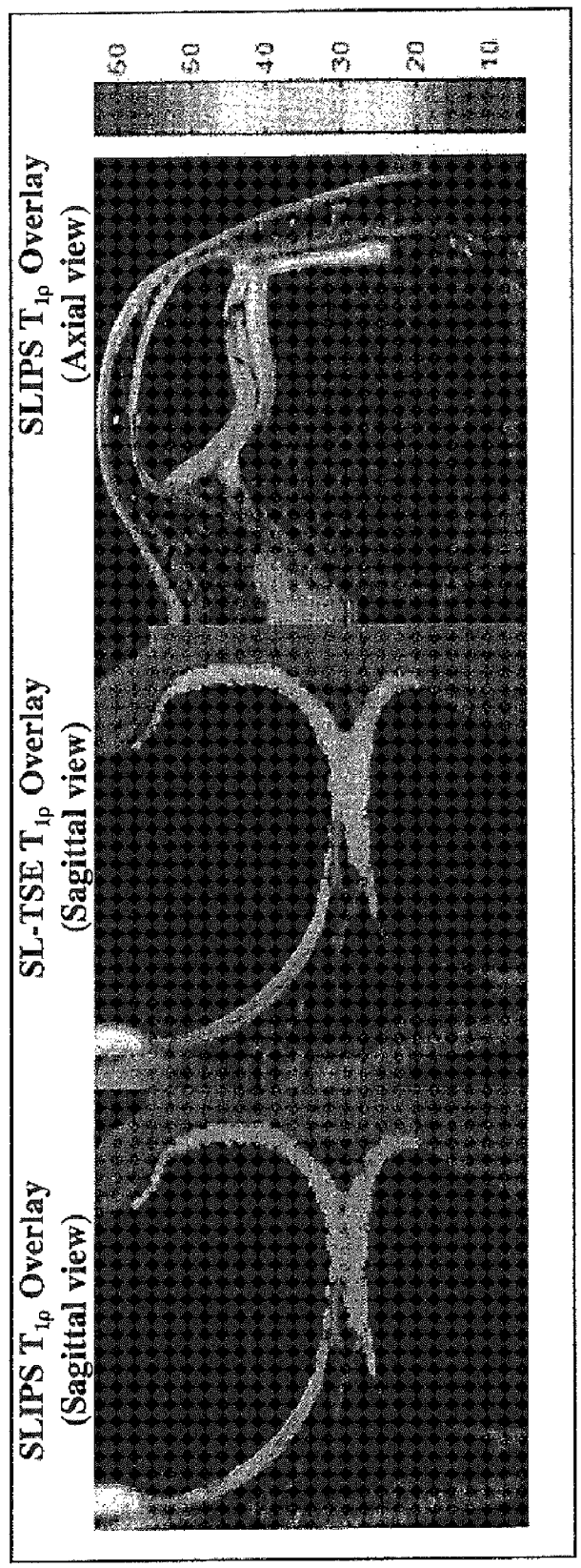
FIG. 10 shows images of the calculated parametric $T_{1\rho}$ value maps for the articular cartilage overlaid onto a $T_2$-weighted image.

Application of the pulse sequence to measure $T_{1\rho}$ in knee cartilage was also demonstrated in this work. Rapid $T_{1\rho}$-acquired images of the knee joint of a healthy volunteer are shown in FIGS. 9A (Sagittal Views) and 9B (Axial Views). Fat-suppressed anatomy is clearly shown in the low TSL images. Higher spin lock duration images are reduced in intensity, but fluid intensity remains very high. The cartilage also retains much of its intensity as it has a higher $T_{1\rho}$ value than the surrounding tissue. The $T_{1\rho}$ map generated from the $T_{1\rho}$-weighted images (FIG. 10, left) show similar values to those obtained by the $T_{1\rho}$-TSE sequence (FIG. 10, center).

Accordingly, the present pulse sequence has the advantage of rapid three-dimensional acquisition of $T_{1\rho}$ data, over the conventional $T_{1\rho}$-prepared TSE sequence. Studies that examine $T_{1\rho}$ of all articular surfaces of cartilage in the knee joint can be performed clinically by using pulse sequence. The pulse sequence scheme used also allows for the addition of more slices in the acquisition volume, without significantly adding to the scan time, since the actual active scanning acquisition time is proportional to the number of slices, but very short in comparison to the delay time during which no acquisition is taking place. Each additional slice will add an additional time $N_{PE}\times$(Short TR) per volume acquisition, where $N_{PE}$ is the number of phase encoding lines per slice.

The disclosure of each patent, patent application and publication cited or described in this document is hereby incorporated herein by reference, in its entirety.

While the foregoing specification has been described with regard to certain preferred embodiments, and many details have been set forth for the purpose of illustration, it will be apparent to those skilled in the art without departing from the spirit and scope of the invention, that the invention may be subject to various modifications and additional embodiments, and that certain of the details described herein can be varied considerably without departing from the basic principles of the invention. Such modifications and additional embodiments are also intended to fall within the scope of the appended claims.

What is claimed is:

1. A method for magnetic resonance imaging, the method comprising:
    1) generating a pulse sequence that includes a $T_{1\rho}$ preparation period, including generating a series of radio frequency (RF) pulses to obtain $T_{1\rho}$ contrast, comprising first preparing a spinlock pulse cluster by:
        applying a first RF pulse for flipping magnetization,
        applying a one or more RF pulses, with different phase combinations, to spin lock and provide the $T_{1\rho}$ contrast; and
        applying another RF pulse to flip the magnetization storage; then
    2) applying at least one additional gradient pulse;
    3) acquiring multiple lines of k-space, and restoring at least part of the $T_{1\rho}$-weighted magnetization created by the spin lock pulse cluster; and then following whole segment acquisition of the k-space,
    4) allowing magnetization to relax toward thermal equilibrium for a time to restore at least partial equilibrium magnetization.

2. A method of using a $T_{1\rho}$ weighted pulse sequence for magnetic resonance imaging as provided according to claim 1, the method of use further comprising:
    generating $T_{1\rho}$ contrast by applying three or more RF pulses, wherein the pulses comprise a first RF pulse, followed by the application of RF spin-locking pulses of any phase, and another final RF pulse (angle $\alpha/2$) prior to applying the at least one excitation pulse and acquiring the multiple lines of k-space data after application of the at least one excitation pulse.

3. The method of claim 2, further comprising applying pre-preparation pulses, gradients and delays before preparing the $T_{1\rho}$ the spinlock pulse cluster.

4. The method of claim 2, further comprising applying post-preparation pulses, gradients and delays after the application of the $T_{1\rho}$ preparation, but prior to image acquisition.

5. The method of claim 4, wherein said spin-locking pulse may range from ±pi from the phase of the first RF pulse.

6. The method of claim 2, further comprising applying post-image acquisition pulses, gradients, and delays.

7. The method of claim 2, wherein the spin locking pulse may be varied in duration and amplitude.

8. A parametric map, calculated from the $T_{1\rho}$ weighted pulse sequence provided by the method of claim 2.

9. A $T_{1\rho}$ dispersion map, calculated from the $T_{1\rho}$ maps obtained with varying spin lock pulse amplitude pulse sequence of claim 2.

10. The method of claim 2, further comprising a time delay inserted after the final ($\alpha/2$) pulse.

11. The method of claim 3, further comprising a time delay inserted before a pre-preparation pulse, wherein the pre-preparation pulse is a pre-preparation saturation pulse.

12. The method of claim 11, further comprising a time delay to reduce specific absorption rate (SAR) of a steady-state free precession pulse sequence.

13. The method of claim 2, wherein the use of the $T_{1\rho}$-weighted pulse sequence comprises an evaluation of pathologies selected from the group consisting of cartilage pathology, arthritis, intervertebral disk pathologies, lower back pain, tumors, Alzheimer's disease, neuro-degeneration, myocardial abnormality, heart disease, and functional imaging.

14. The method of claim 1, further comprising a time delay inserted before the pulse cluster.

* * * * *